United States Patent
Johnson et al.

(10) Patent No.: US 10,765,410 B2
(45) Date of Patent: Sep. 8, 2020

(54) SYSTEMS AND METHODS FOR REAL-TIME BIOPSY NEEDLE AND TARGET TISSUE VISUALIZATION

(71) Applicant: Boston Scientific Scimed, Inc., Maple Grove, MN (US)

(72) Inventors: Austin G. Johnson, Hudson, MA (US); Sean Fleury, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 222 days.

(21) Appl. No.: 15/833,381

(22) Filed: Dec. 6, 2017

(65) Prior Publication Data

US 2018/0153530 A1    Jun. 7, 2018

Related U.S. Application Data

(60) Provisional application No. 62/430,987, filed on Dec. 7, 2016.

(51) Int. Cl.

| | |
|---|---|
| *A61B 10/02* | (2006.01) |
| *A61B 8/08* | (2006.01) |
| *A61B 8/12* | (2006.01) |
| *A61B 10/04* | (2006.01) |
| A61B 17/34 | (2006.01) |
| A61B 90/00 | (2016.01) |

(52) U.S. Cl.
CPC ........ *A61B 10/0275* (2013.01); *A61B 8/0841* (2013.01); *A61B 8/12* (2013.01); *A61B 8/483* (2013.01); *A61B 10/0283* (2013.01); *A61B 10/04* (2013.01); *A61B 8/085* (2013.01); *A61B 2010/0208* (2013.01); *A61B 2017/3413* (2013.01); *A61B 2090/378* (2016.02)

(58) Field of Classification Search
None
See application file for complete search history.

(56) References Cited

U.S. PATENT DOCUMENTS

| | | | | |
|---|---|---|---|---|
| 5,345,940 | A * | 9/1994 | Seward | A61B 8/06 600/439 |
| 5,671,748 | A * | 9/1997 | Itoi | A61B 1/00165 600/117 |
| 5,873,828 | A * | 2/1999 | Fujio | A61B 1/0051 600/439 |
| 6,296,608 | B1 * | 10/2001 | Daniels | A61B 1/00165 600/104 |
| 7,507,205 | B2 * | 3/2009 | Borovsky | A61B 8/12 600/466 |
| 2002/0026127 | A1 * | 2/2002 | Balbierz | A61B 5/0071 600/567 |

(Continued)

FOREIGN PATENT DOCUMENTS

WO    2016067886 A1    5/2016

OTHER PUBLICATIONS

International Search Report and Written Opinion dated (Mar. 1, 2018), for PCT/US17/64881 (11 pages).

*Primary Examiner* — Michael R Bloch

(57) ABSTRACT

The present disclosure relates to the field of endoscopy. In particular, the present disclosure relates to systems and methods for real-time visualization of a target tissue, and which allows the location/orientation of the biopsy needle to be determined prior to its first actuation.

20 Claims, 14 Drawing Sheets

(56) References Cited

U.S. PATENT DOCUMENTS

| | | | |
|---|---|---|---|
| 2004/0077927 A1* | 4/2004 | Ouchi | A61B 1/00142 |
| | | | 600/123 |
| 2005/0256426 A1 | 11/2005 | Brugge | |
| 2006/0116605 A1* | 6/2006 | Nakao | A61B 10/0266 |
| | | | 600/566 |
| 2009/0281429 A1 | 11/2009 | Nishina et al. | |
| 2010/0063401 A1* | 3/2010 | Nishina | A61B 1/018 |
| | | | 600/466 |
| 2011/0152610 A1* | 6/2011 | Trusty | A61B 1/0008 |
| | | | 600/104 |
| 2011/0251458 A1 | 10/2011 | Terliuc et al. | |
| 2015/0328434 A1* | 11/2015 | Gaur | A61M 5/427 |
| | | | 600/424 |

\* cited by examiner

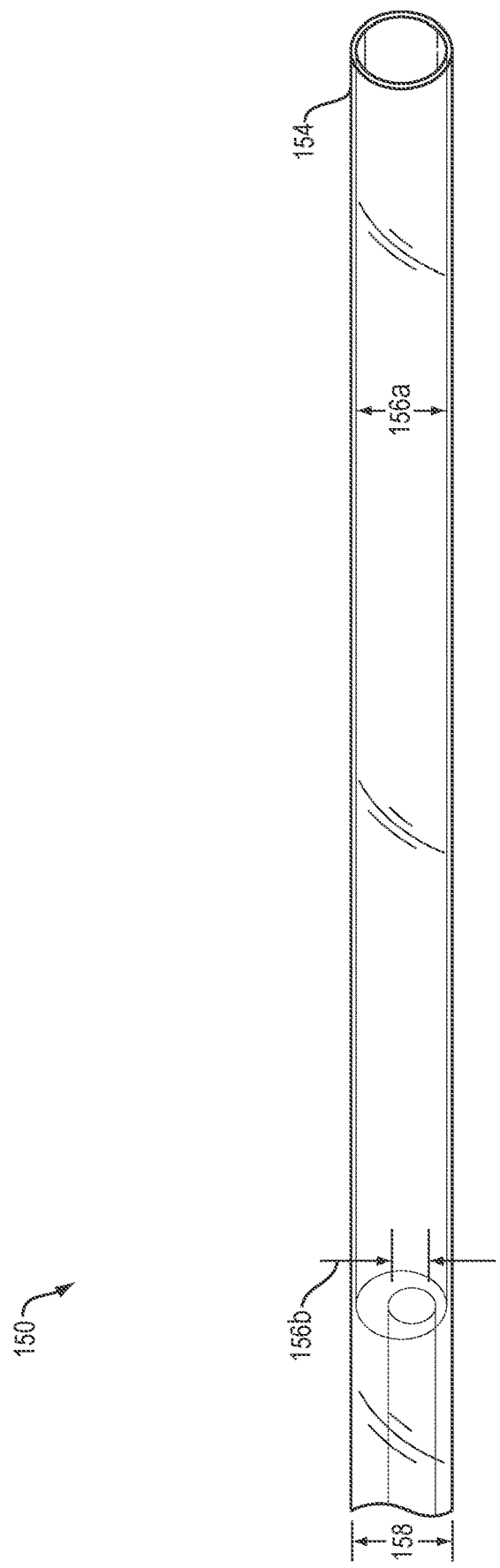

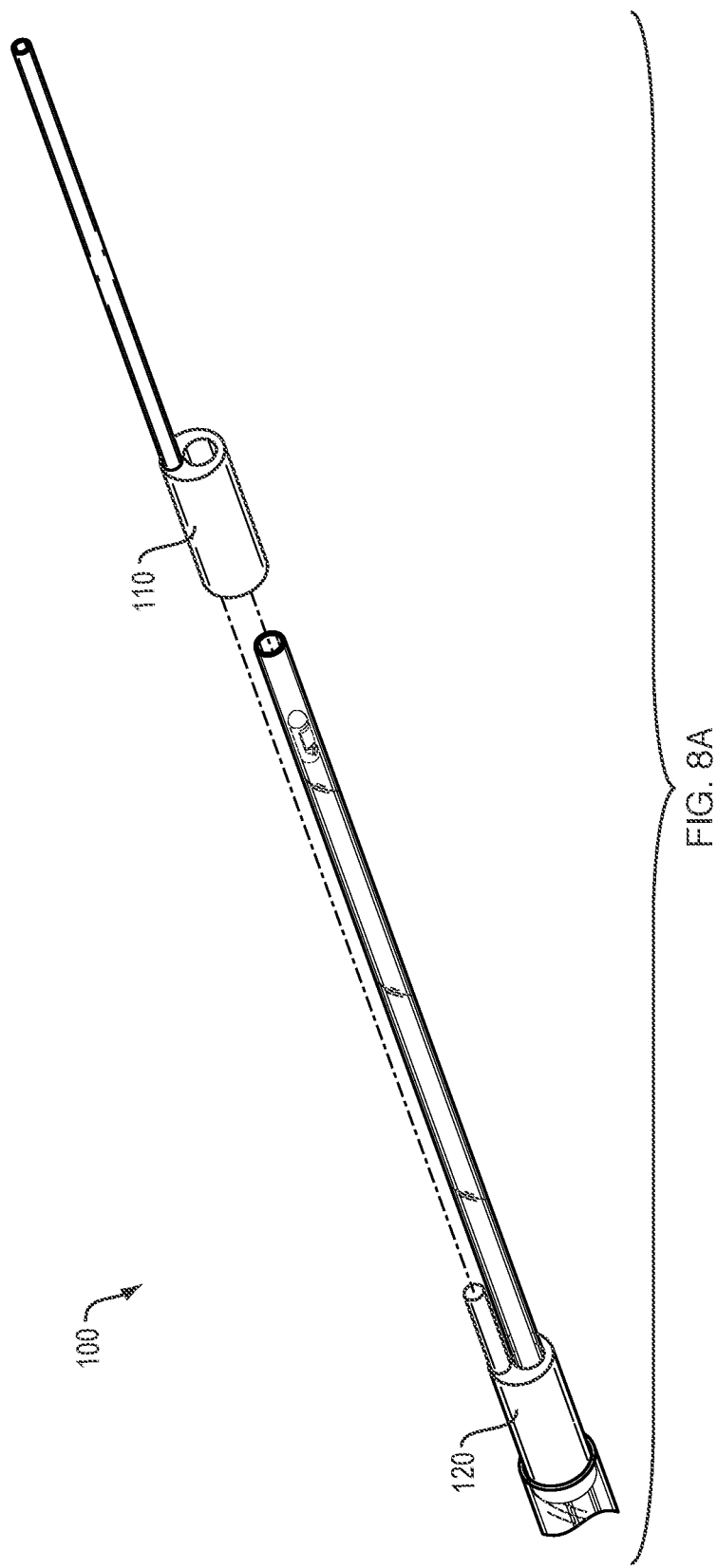

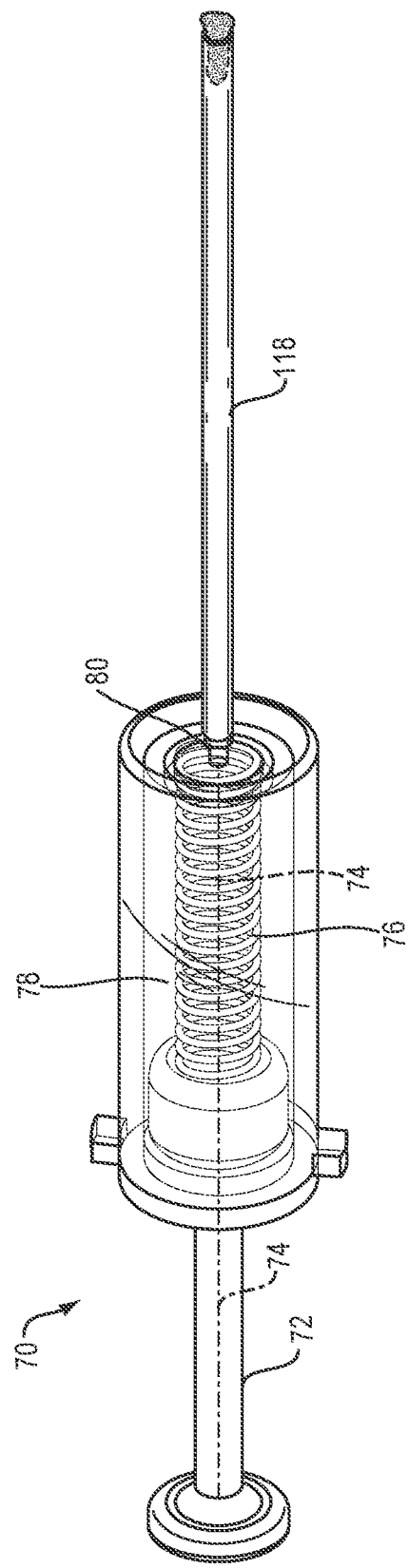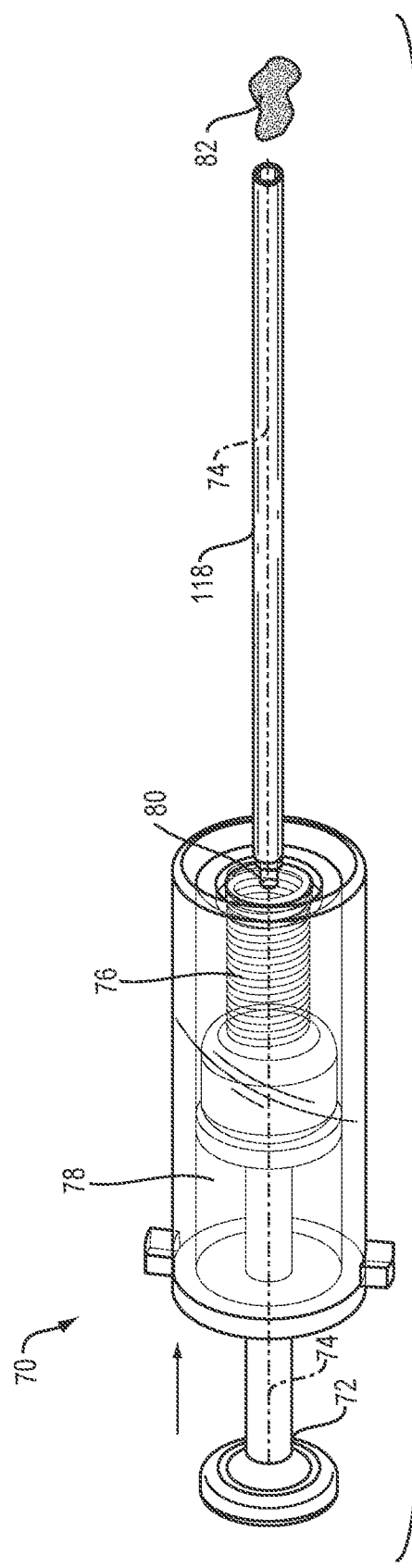

SYSTEMS AND METHODS FOR REAL-TIME BIOPSY NEEDLE AND TARGET TISSUE VISUALIZATION

CROSS REFERENCE TO RELATED APPLICATIONS

The present application claims the benefit of priority under 35 U.S.C. § 119 to U.S. Provisional Patent Application Ser. No. 62/430,987, filed on Dec. 7, 2016, which is incorporated by reference in its entirety for all purposes.

FIELD

The present disclosure relates to the field of endoscopy. In particular, the present disclosure relates to systems and methods which allow for real-time visualization of a target tissue, and which allow for efficient and accurate location/orientation of a biopsy needle prior to its first actuation and sample acquisition.

BACKGROUND

Radial endobronchial ultrasound (R-EBUS) provides a minimally invasive option when clinical presentation indicates that tissue biopsy within the pulmonary passages is necessary. Conventional R-EBUS transbronchial needle aspiration (TBNA) involves delivering a radial ultrasound probe to the target airway through the working channel of a bronchoscope, visualizing the target pulmonary nodule on R-EBUS, locking placement of an access sheath, removing the radial ultrasound probe from the access sheath and then blindly advancing a biopsy needle to acquire cellular matter for cytologic evaluation. The inability to visualize the biopsy needle until after the tissue sampling procedure has been initiated often results in the biopsy needle completely missing the target nodule. To help ensure that the target nodule is successfully biopsied, the medical professional typically actuates the biopsy needle into the pulmonary tissue multiple times while rotating the bronchoscope. Such repetitive biopsy needle actuations may result in a variety of negative medical outcomes, including, unnecessary trauma to healthy tissues, excessive bleeding, pleural sac punctures (e.g., pneumothorax), blood vessel punctures, increased procedure duration and/or cost and potentially misdiagnosis (e.g., false-negatives).

There may be a clinical advantage, particularly in the field of pulmonary endoscopy, for a tissue sampling system which allows a medical professional to visualize a biopsy needle and target tissue in real-time prior to the first needle actuation.

SUMMARY

The present disclosure, in its various aspects, provides advantages in the medical field, such as the field of pulmonary endoscopy, for a sampling system that allows real-time visualization of pulmonary nodules, and which allows the location/orientation of the biopsy needle to be efficiently and accurately determined prior to its first actuation and sample acquisition.

In one aspect, the present disclosure relates to a device comprising a first component that includes a proximal end, a distal end, and a lumen extending therebetween, and a tissue sampling element attached to the distal end of the first component. The proximal end of the first component may include a recessed portion. The tissue sampling element may include, e.g., a biopsy needle. The tissue sampling element may include a substantially linear configuration. The tissue sampling element may be moveable between a substantially linear configuration and a substantially curved configuration.

In another aspect, the present disclosure relates to a system comprising a first component that includes a proximal end, a distal end, and a lumen extending therebetween, and a second component that includes a proximal end, a distal end, and a lumen extending therebetween. The proximal end of the first component may be removably attached to the distal end of the second component to form a contiguous lumen. An ultrasound catheter may extend through the contiguous lumen of the first and second components. An exterior tube may be slidably disposed about the first component, second component and ultrasound catheter. The ultrasound catheter may include an ultrasound probe slidably disposed within a sheath which forms an interference fit with the lumen of the second component. A tissue sampling element may be attached to the distal end of the first component. The proximal end of the first component may include a recessed portion configured to receive a post extending from a distal end of the second component. The post of the second component may form an interference fit with the recessed portion of the first component. The lumen of the first component may align with the lumen of the second component to form a contiguous lumen when the post is disposed within the recessed portion. A portion of the sheath may extend distally beyond the ultrasound probe. A portion of the sheath may include a braided material. The braided material may extend along a proximal portion of the ultrasound probe. The portion of the sheath that extends distally beyond the ultrasound probe may include an unbraided material. The sheath may include a proximal end, a distal end and a lumen extending therebetween. The lumen of the sheath may include a first diameter portion and a second diameter portion. The system may further comprise a delivery device that includes a working channel configured to slidably receive the exterior tube. A proximal end of the ultrasound probe may be connected to a motor drive unit. The system may further include a delivery device comprising a working channel configured to slidably receive the exterior tube.

In another aspect, the present disclosure relates to a method comprising advancing a tissue sampling system through a body passage, wherein the tissue sampling system includes interlocked first and second components removably disposed about an ultrasound catheter; imaging, with the ultrasound catheter, a target tissue with the body passage; advancing the tissue sampling system such that a portion of the first component penetrates the target tissue; and withdrawing the tissue sampling system from the body passage. The method may further comprise, prior to advancing the tissue sampling system, rotating the tissue sampling system to align the first component with the target tissue. The tissue sampling system may be advanced simultaneous with the imaging of the target tissue.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIG. 6 provides a schematic view of a distal portion of an exterior tube, according to one embodiment of the present disclosure.

FIGS. 8A-8C illustrate the steps involved in removing a tissue sample from a tissue acquisition element, according to one embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to real-time visualization and sampling of pulmonary nodules, the systems and methods disclosed herein may be used to obtain biopsy samples from within a variety of body lumens, including, for example, the heart, vascular system, circulatory system, gastrointestinal (GI) tract, stomach, esophagus, urogenital system and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from a medical professional when introducing a device into a patient, while the term "proximal" refers to the end closest to the medical professional when introducing a device into a patient.

The present disclosure generally provides a tissue sampling system that includes a sampling component reversibly (e.g., removably) connected to an ultrasound catheter by a keyed or press-fit interaction with a connector component attached to an outer surface of the ultrasound catheter. The coupling geometry of the connector component and sampling component prevents rotation and/or translation of the sampling component relative to the ultrasound catheter and provides a fixed alignment which allows the medical professional to know in which quadrant of the radial ultrasound image the sampling component will appear relative to the target nodule prior to each tissue sampling step.

Figure 1:
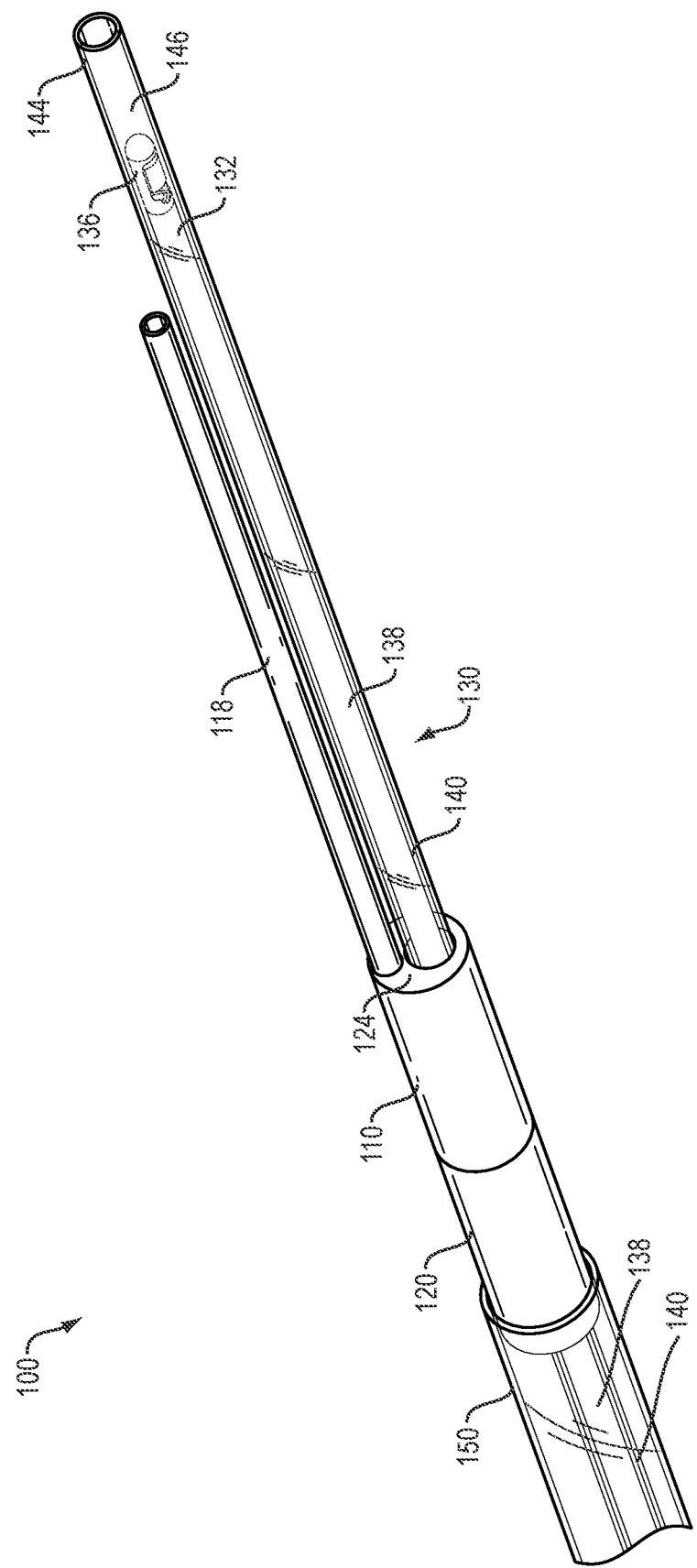
FIG. 1 provides a schematic view of a tissue sampling system, according to one embodiment of the present disclosure.

Referring to FIG. 1, in one embodiment, the present disclosure provides a tissue sampling system 100 comprising a first component 110 (e.g., sampling component) and a second component 120 (e.g., connector component) disposed about an ultrasound catheter 130 (e.g., radial ultrasound catheter). The first component 110 may further include a tissue sampling element 118 (e.g., biopsy needle, fine aspiration needle, biopsy brush, etc.) extending from the distal end 124. An exterior tube 150 may be slidably disposed about the ultrasound catheter 130 and first and second components 110, 120. The ultrasound catheter 130 may include an ultrasound transducer 136 disposed at the distal end 132 of an ultrasound probe 138 (e.g., radial ultrasound probe). The ultrasound transducer 136 and ultrasound probe 138 may be slidably disposed within a sheath 140 that includes a proximal end (not depicted), distal end 144 and a lumen 146 extending therebetween. A proximal end (not depicted) of the ultrasound probe 138 may be attached to a motor drive unit (MDU) configured to advance (e.g., move distally) and retract (e.g., move proximally) the ultrasound probe 138 and ultrasound transducer 136 within the fixed sheath 140. The sheath 140 may be formed from a variety of materials that provide the requisite mechanical properties to navigate through narrow and tortuous body passages.

In the various embodiments, the position of the first and second components 110, 120 about the ultrasound catheter 130 may provide a distinct advantage over conventional tissue sampling systems due to the close proximity of the tissue sampling element 118 to the ultrasound transducer 136. Specifically, configurations such as depicted may allow the tissue sampling element 118 to be positioned in close proximity to the target tissue (e.g., within 5 mm or less) as the radial ultrasound image of the target tissue is being generated (e.g., in real-time). The close proximity to the target tissue allows that tissue sampling element 118 to be much shorter than conventional biopsy needles. For example, while a conventional pulmonary biopsy needle may include a length of 50 centimeters or more, the tissue sampling element of the present disclosure may include a length of less than 25 cm (e.g., 20 cm or less, 15 cm or less, 10 cm or less, 5 cm or less, 2.0 cm or less). The dramatically shorter length of the tissue sampling element 118 allows for lower production costs, and also allows more reliable and accurate sampling of the target tissue.

Figure 2:
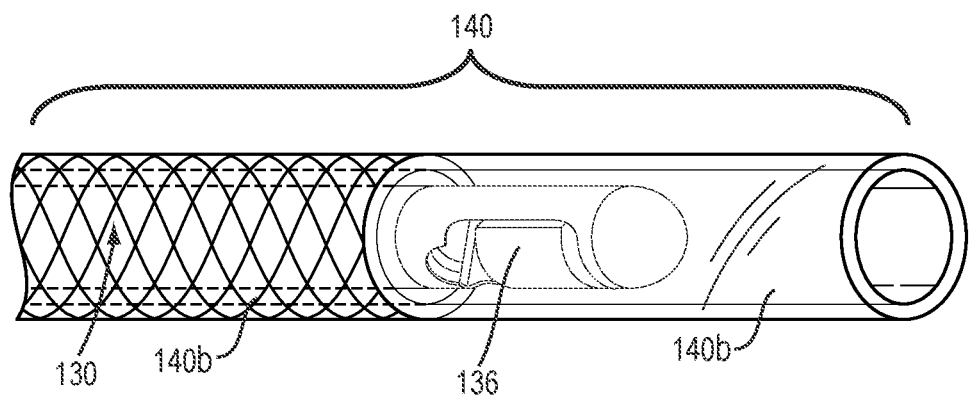
FIG. 2 provides a schematic view of a distal portion of an ultrasound catheter, according to one embodiment of the present disclosure.

As illustrated in FIG. 2, a portion of the sheath 140 extending proximally from the ultrasound transducer 136 may include a braided material 140a (e.g., interwoven strands of flexible polymeric, carbon fiber, metallic and/or textile materials etc.) which provides enhanced stiffness (e.g., pushability) and torqueability to allow the ultrasound catheter 130 and the first and second components attached to the sheath 140 to be distally advanced and proximally retracted within and through the exterior tube by actuating (e.g., pushing and pulling) a proximal end (not depicted) of the sheath 140. In addition, or alternatively, a portion of the sheath 140 extending distally beyond the ultrasound transducer 136 may include an unbraided material 140b (e.g., clear plastic, silicone and/or rubber materials, etc.) that does not influence ultrasound image quality and target nodule visualization, while providing a conduit through which a suitable fluid (e.g., isotonic saline, etc.) may be intermittently flushed for consistent and reliable propagation of ultrasound energy. The unbraided material 140b may also provide sufficient flexibility and/or deformability to bend or deflect during the tissue acquisition step such that the tissue sampling element is not impeded or obstructed from penetrating the target nodule.

In one embodiment, a portion of the sheath 140 extending distally beyond the ultrasound transducer 136 may include a "strip" of hyperechoic (e.g., radiopaque) material, which appears as a dark portion (e.g., slice) on the radial ultrasound image. For example, the hyperechoic material may include a suitable powdered material (e.g., barium sulfate, etc.) mixed into the polymeric material(s) comprising the sheath 140 prior to the extrusion process. In addition, or alternatively, the hyperechoic material may include a thin strip of metallic material (e.g., copper, brass, stainless steel etc.) embedded within or otherwise adhered and/or affixed to a portion of the sheath 140 extending distally beyond the ultrasound transducer 136. Because the first component 110 and sheath 140 are fixed to each other both axially and rotationally, and the orientation of the ultrasound catheter 130 is fixed rotationally with respect to the first component 110, the location of the hyperechoic strip on the radial ultrasound image may allow a medical professional to identify the relative location of the tissue sampling element 118 even if the tissue sampling element is positioned behind (e.g., proximal to) the ultrasound transducer 136. For example, the "strip" of hyperechoic material may be disposed on a portion of the sheath 140 that is directly opposite (e.g., offset 180 degrees) from the tissue sampling element. While visualizing the radial ultrasound image, the exterior tube 150 of the tissue sampling system 100 may be rotated in real-time to position the "strip" of hyperechoic material directly opposite the target nodule prior to distally advancing the ultrasound probe to deliver the tissue sampling element 118 into the target nodule.

Figure 3:
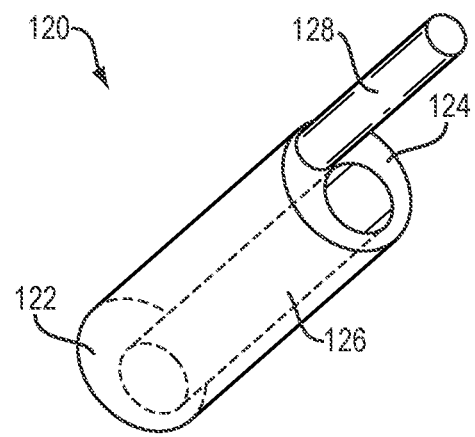
FIG. 3 provides a schematic views of a connector component, according to one embodiment of the present disclosure.
Figure 4A:
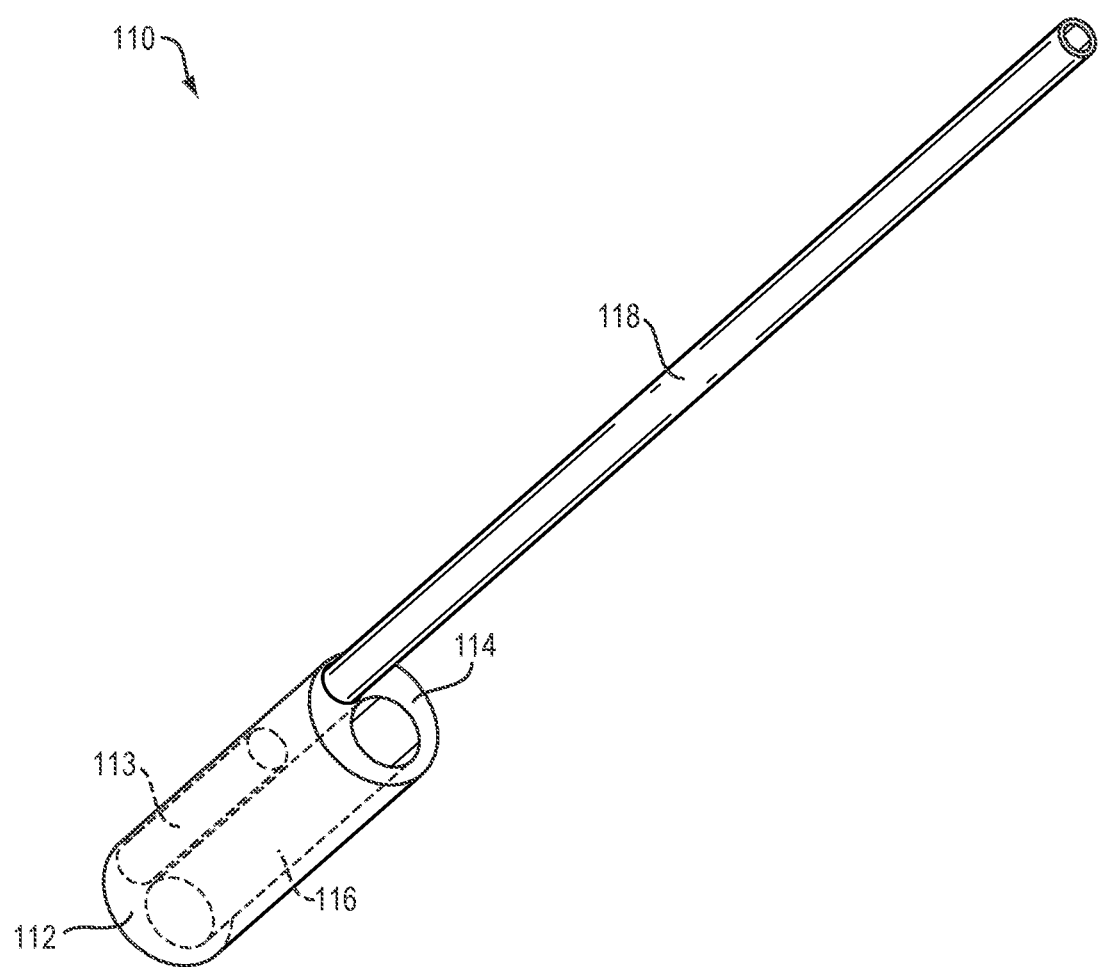
FIGS. 4A-4B provide schematic views of a sampling component that includes a straight (FIG. 4A) or curved (FIG. 4B) tissue acquisition element, according to one embodiment of the present disclosure.
Figure 4B:
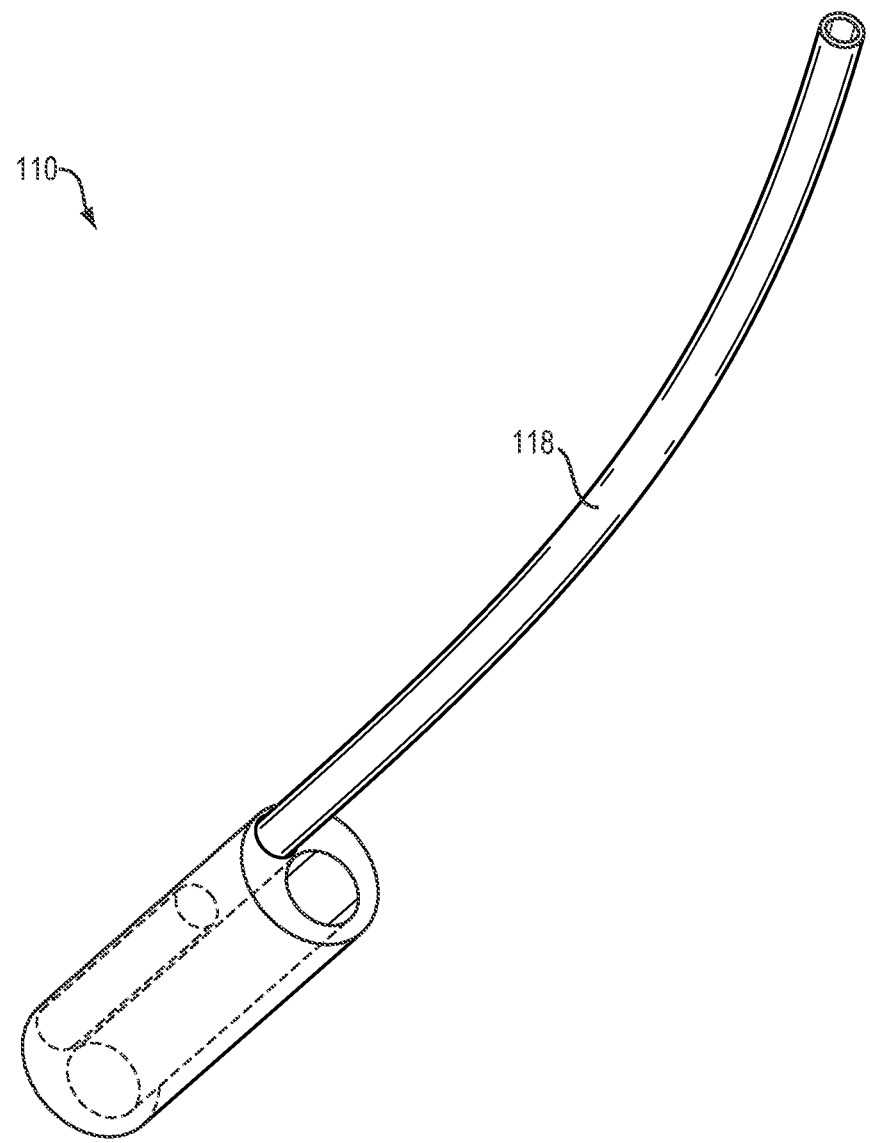
Figure 5:
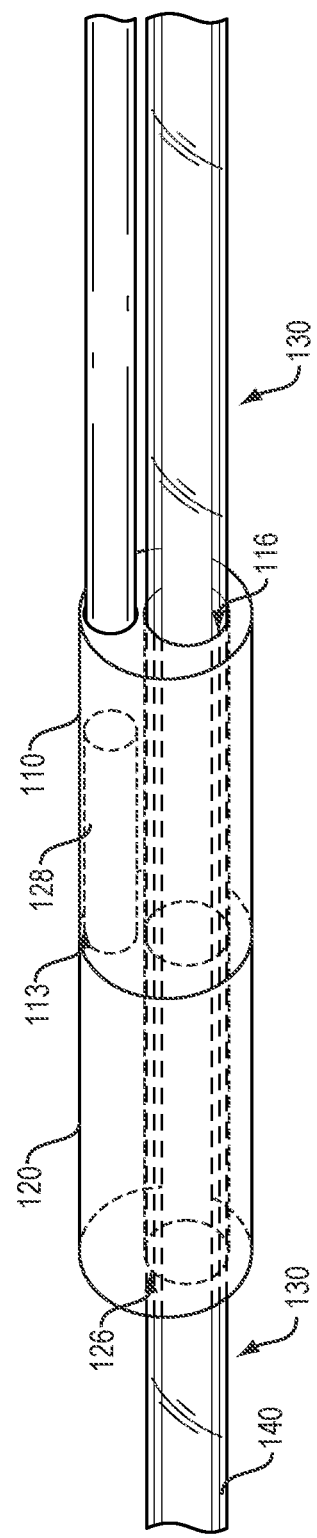
FIG. 5 provides an enlarged schematic view of a connector component and sampling component interlocked onto an ultrasound catheter, according to one embodiment of the present disclosure.

FIG. 3 provides an isolated schematic view of the second component 120 of FIG. 1. The second component 120 may include a proximal end 122, distal end 124 and lumen 126 extending therebetween. The second component 120 may further include a post 128 (e.g., arm, tab, etc.) extending from the distal end 124. FIG. 4A provides an isolated schematic view of the first component 110 of FIG. 1. The first component 110 may include a proximal end 112, distal end 114 and lumen 116 extending therebetween. The proximal end 112 may include a recessed portion 113 (e.g., pocket etc.) configured to receive the post 128 of second component 120 in a keyed or press-fit manner to interlock the first and second components 110, 120 together (FIG. 5). In some embodiments, recessed portion 113 may be a through lumen that extends from the proximal end of the first component 110 to the proximal end of the sampling element 118 to provide a contiguous lumen for extracting the sample once acquired, as described further below. The first component 110 may further include a substantially straight tissue sampling element 118 (e.g., biopsy needle, fine aspiration needle, biopsy brush etc.) extending from the distal end 124 for sampling a concentric target nodule. Alternatively, as illustrated in FIG. 4B, the first component 110 may include a tissue sampling element 118 configured to move from a straight to bent configuration when advanced distally beyond, and released from constraint within, the exterior tube for sampling an eccentric target nodule. The tissue sampling elements of FIGS. 4A and 4B may be embedded within the materials which form the first component, e.g., during the polymer co-extrusion process and/or secured using a suitable resin, glue or epoxy etc. Alternatively, the tissue sampling element 118 may be removable from the first component after tissue acquisition in order to remove the sample with another device such as described below.

Referring to FIG. 5, the second component 120 may be attached to a distal portion of the sheath 140 of the ultrasound catheter 130 by advancing (e.g., sliding) the ultrasound catheter through the lumen 126 of the second component 120 to form an interference fit between an outer surface of the sheath 140 and an inner surface of the lumen 126. The interference fit between the second component 120 and the outer surface of sheath 140 may be sufficiently strong to prevent the second component from moving axially and/or rotationally along the ultrasound catheter 130 during a medical procedure, but sufficiently weak that a medical professional may move (e.g., reposition) or remove (e.g., detach or separate) the second component 120 by applying simultaneous twisting and pulling/pushing forces with one (or both) hands. Alternatively, the second component 120 may be permanently affixed to the sheath 140 of the ultrasound catheter 130 by a suitable weld, solder, braze, adhesive, glue and/or resin. Still referring to FIG. 5, with the second component 120 firmly attached to the ultrasound catheter 130, the first component 110 may be advanced over a distal portion of the ultrasound catheter 130 such that the recessed portion 113 of the first component 110 receives, and forms an interference fit (e.g., keyed fit, or press-fit) with, the post 128 of the second component 120. The interference fit between the recessed portion 113 and post 128 may establish a reversible interlock which properly aligns and couples the first and second components 110, 120 to prevent radial and/or axial movement of the first component 110 relative to sheath 140 of the ultrasound catheter 130 throughout the duration of the medical procedure. Rotational and/or axial movement of the first component 110 along and/or about the sheath 140 of the ultrasound catheter 130 may be further restricted by frictional forces between the outer surface of the sheath 140 and inner wall of the lumen 116. As above, the combined interference fit(s) between the first component 110, second component 120 and ultrasound catheter 130 (e.g., outer surface of sheath 140) may be sufficiently strong to prevent the first component from moving axially and/or rotationally along the ultrasound catheter 130 during a medical procedure (e.g., within the patient), but sufficiently weak that a medical professional may remove or detach the first component 110 from the second component 120 and ultrasound catheter 130 by applying sufficient force (e.g., twisting and/or pulling) with one (or both) hands.

Referring to FIG. 6, in one embodiment, the exterior tube 150 may include a proximal end (not depicted), a distal end 154 and a variable-diameter lumen extending therebetween. For example, a distal portion of the exterior tube 150 may include a lumen with first diameter 156a configured to receive and protect (e.g., fit over) the second component 120, first component 110 and ultrasound catheter 130. The remaining portion of the exterior tube 150 may include a second diameter 156b, smaller than the first diameter 156a and configured to slidably receive the ultrasound catheter. The smaller second diameter 156b may provide increased wall thickness to the exterior tube 150 for improved pushability, steerability and resistance to bending and/or kinking. In addition, or alternatively, the smaller diameter second diameter 156b may constrain the ultrasound catheter along its length to prevent excessive bending within the exterior tube as the tissue sampling system is advanced through narrow and tortuous body passages. The exterior tube 150 may be formed from a variety of materials that provide the requisite mechanical properties (e.g., stiffness, pushability, flexibility, torqueability) to navigate through tortuous body passages without bending, kinking and/or breaking. The exterior tube 150 may further include one or more braided materials (e.g., interwoven strands of flexible polymeric, carbon fiber, metallic and/or textile materials etc.) to provide enhanced stiffness, torqueability and/or flexibility along all (or a portion of) the exterior tube. The exterior tube may include an outer diameter 158 configured to pass through the working channel of a conventional bronchoscope (e.g., approximately 2.0 mm to approximately 4.0 mm). The exterior tube 150 is in no way limited to a dual-diameter lumen, but may include a variety of lumen diameters, including, but not limited to single-diameter lumens, tapered-diameter lumens and the like.

Figure 7A:
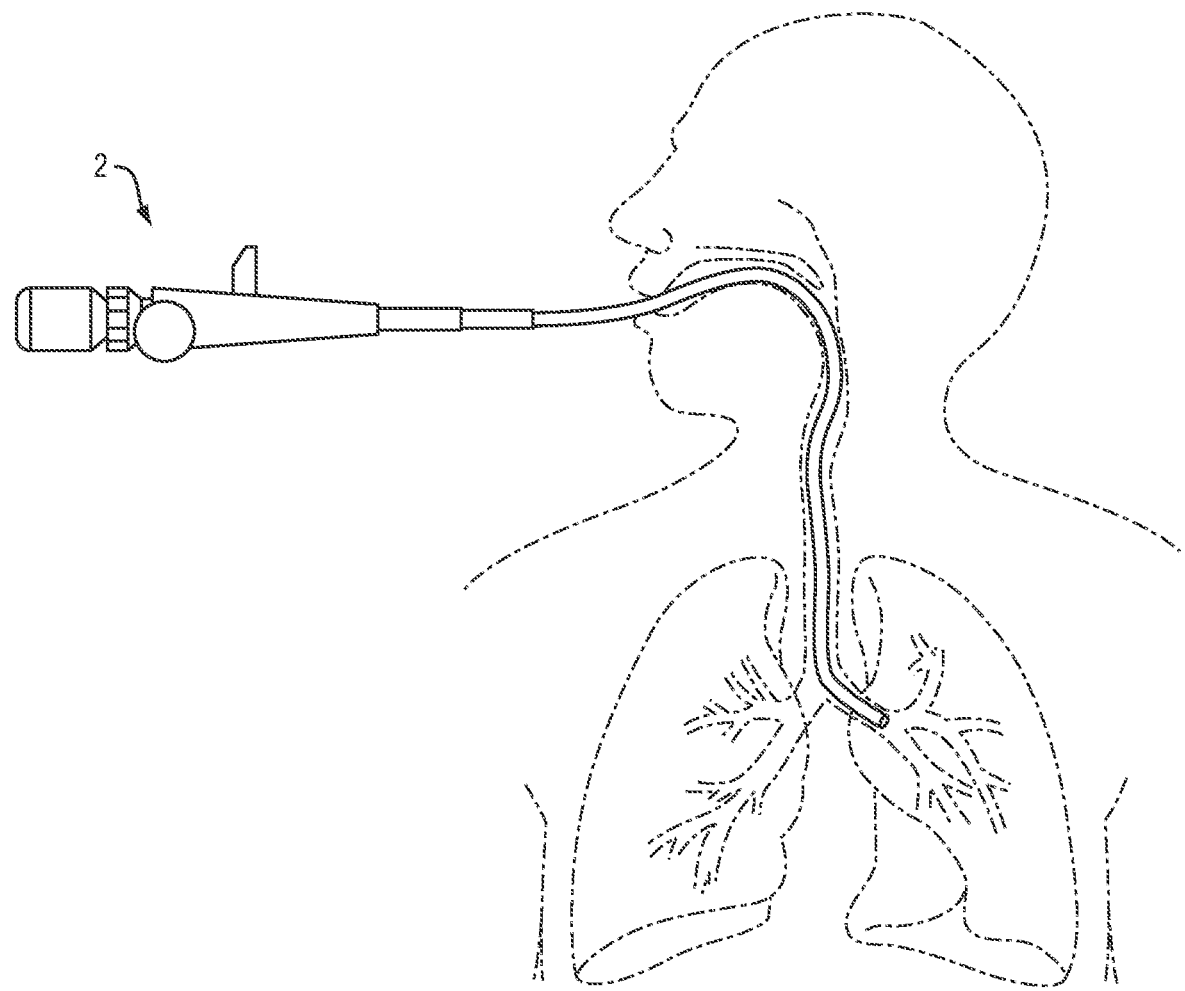
FIGS. 7A-7F illustrate the steps involved in sampling a pulmonary nodule, according to one embodiment of the present disclosure.
Figure 7B:
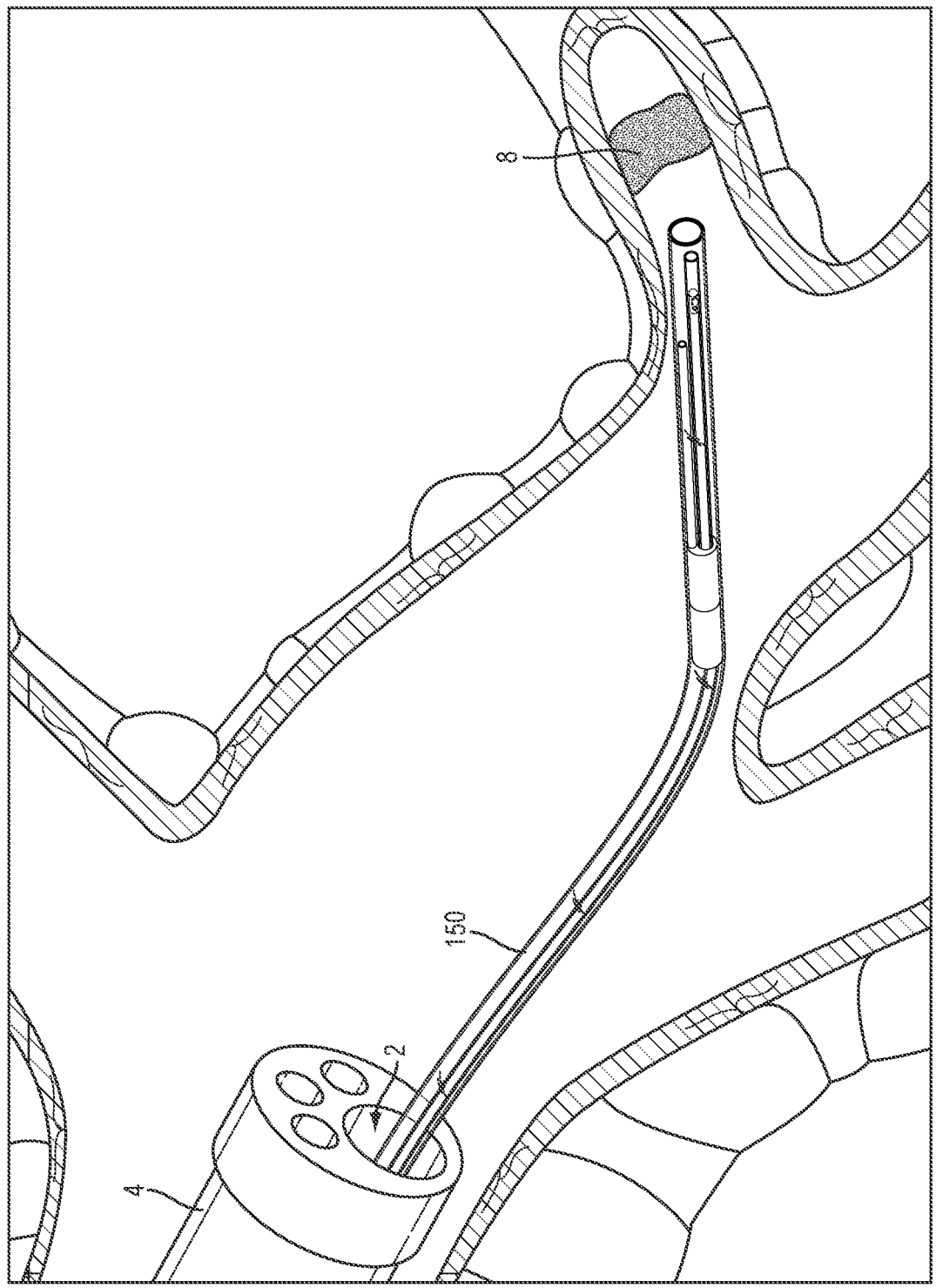
Figure 7C:
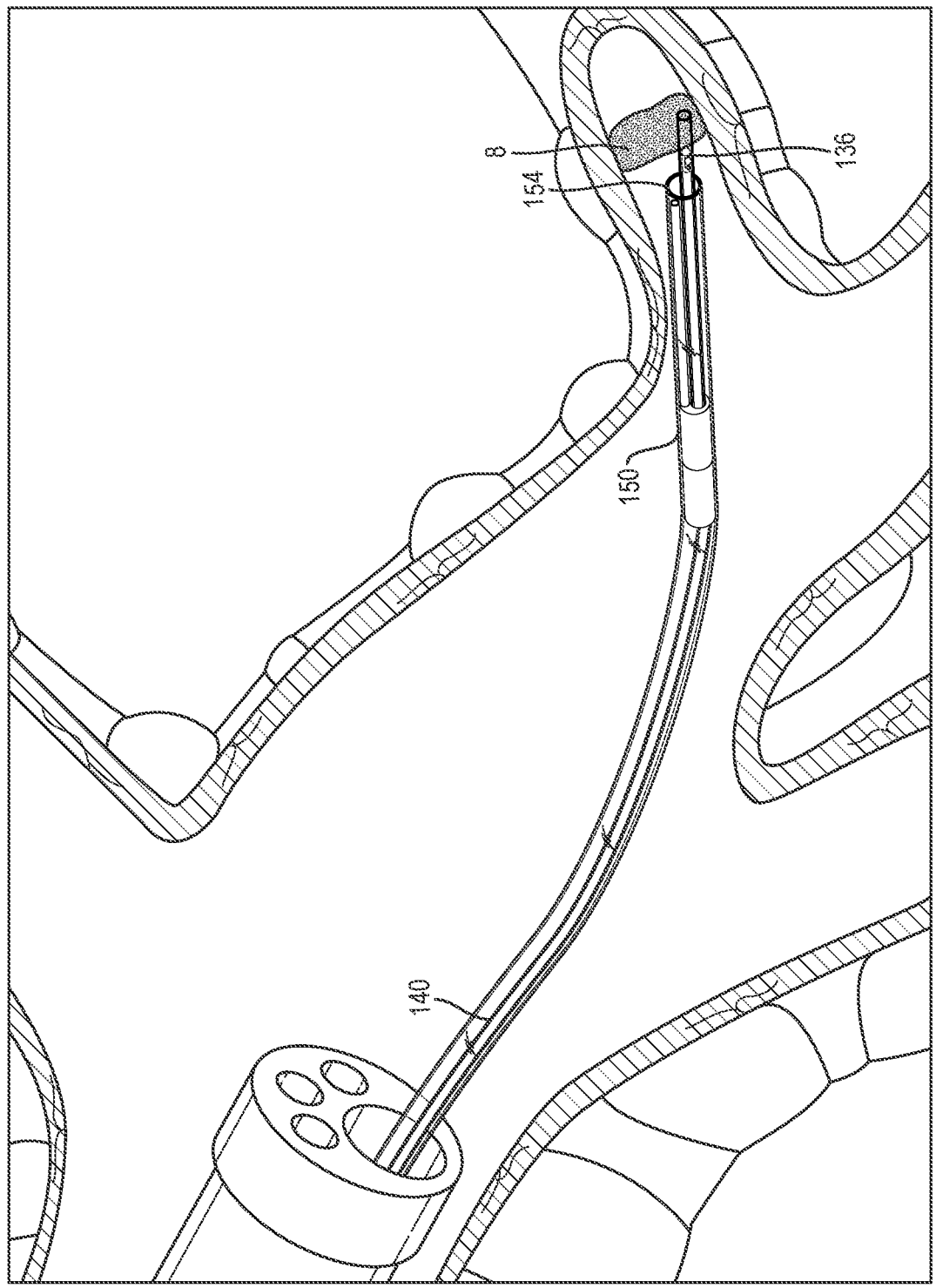
Figure 7D:
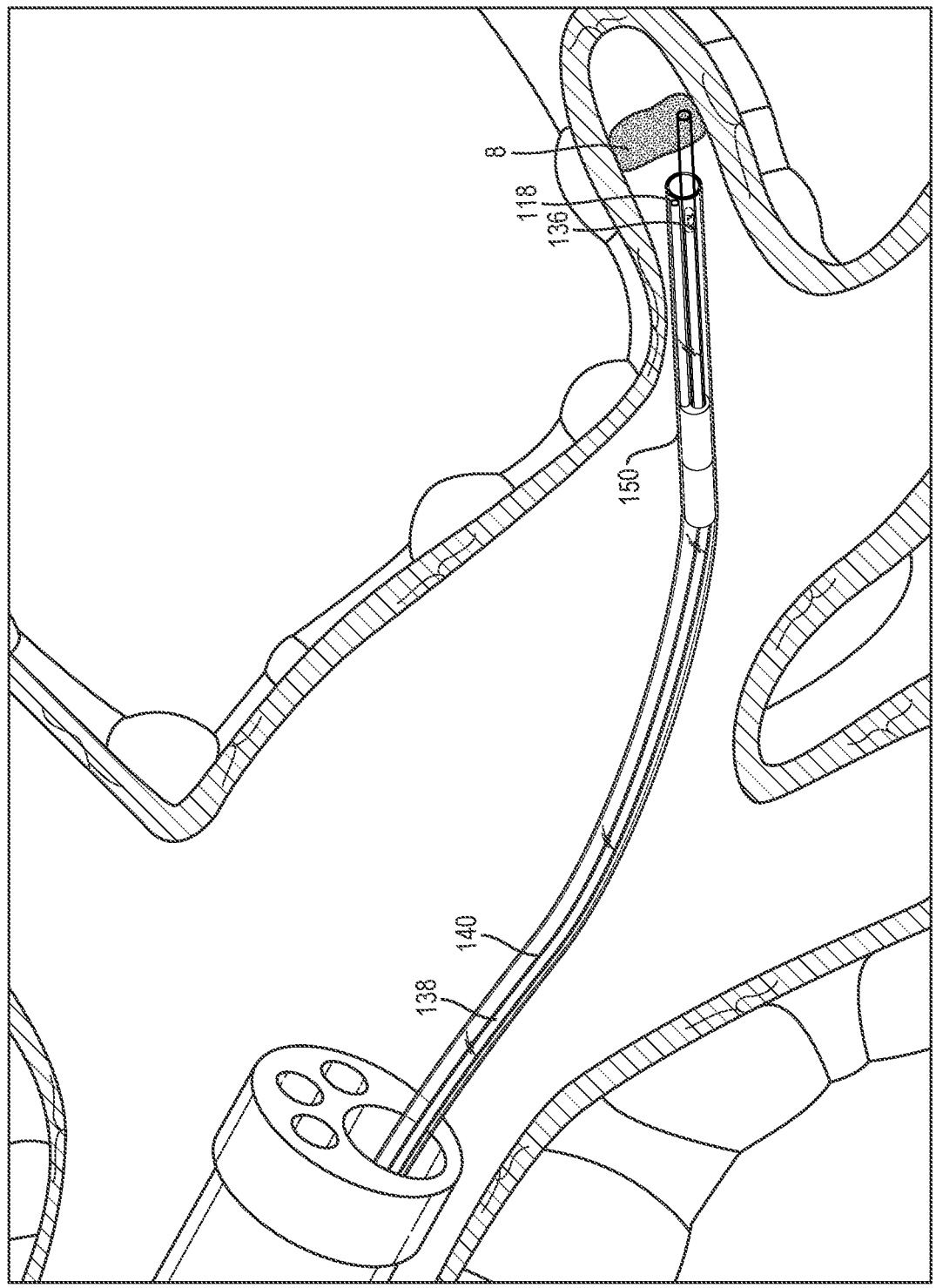
Figure 7E:
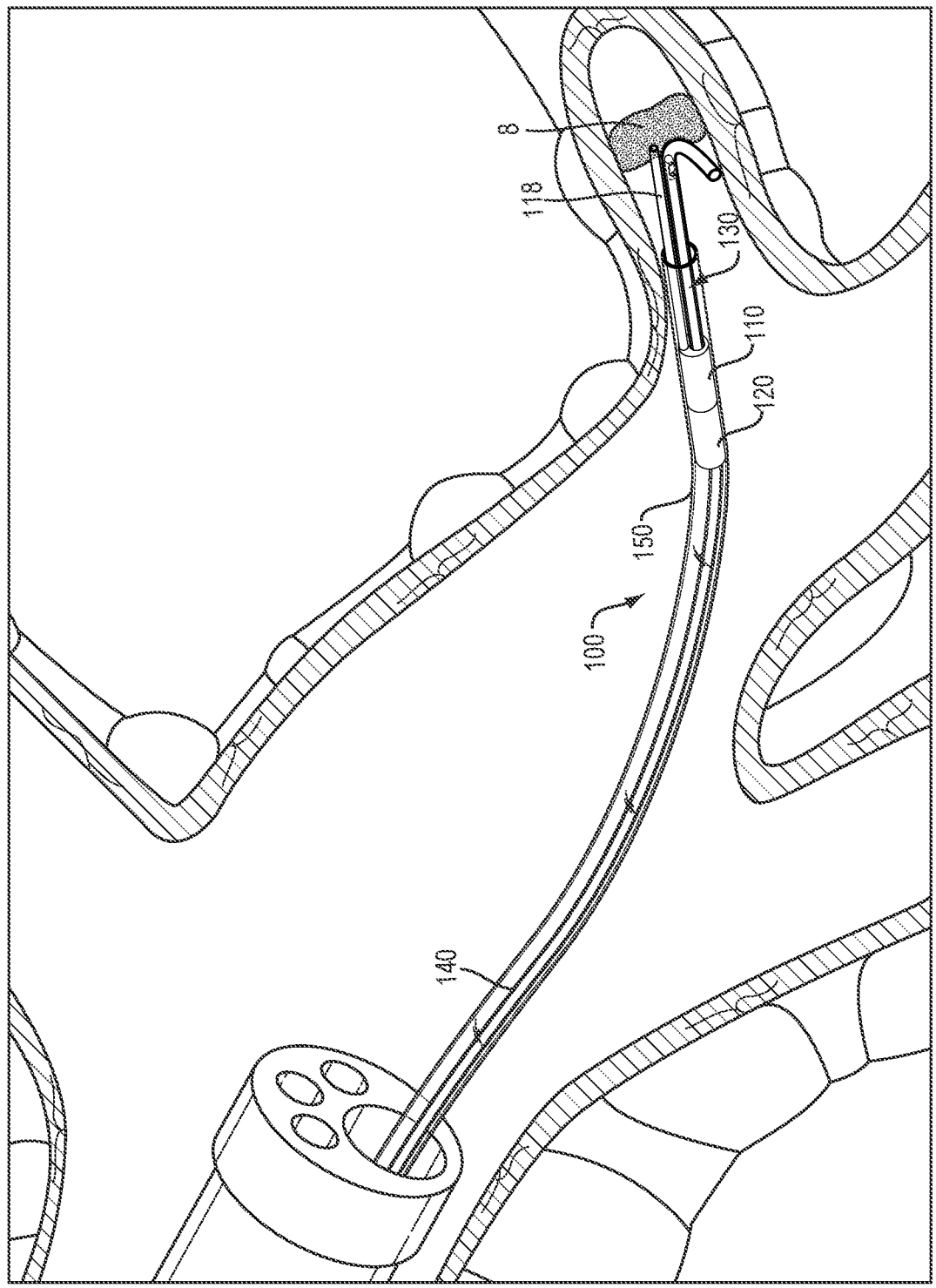
Figure 7F:
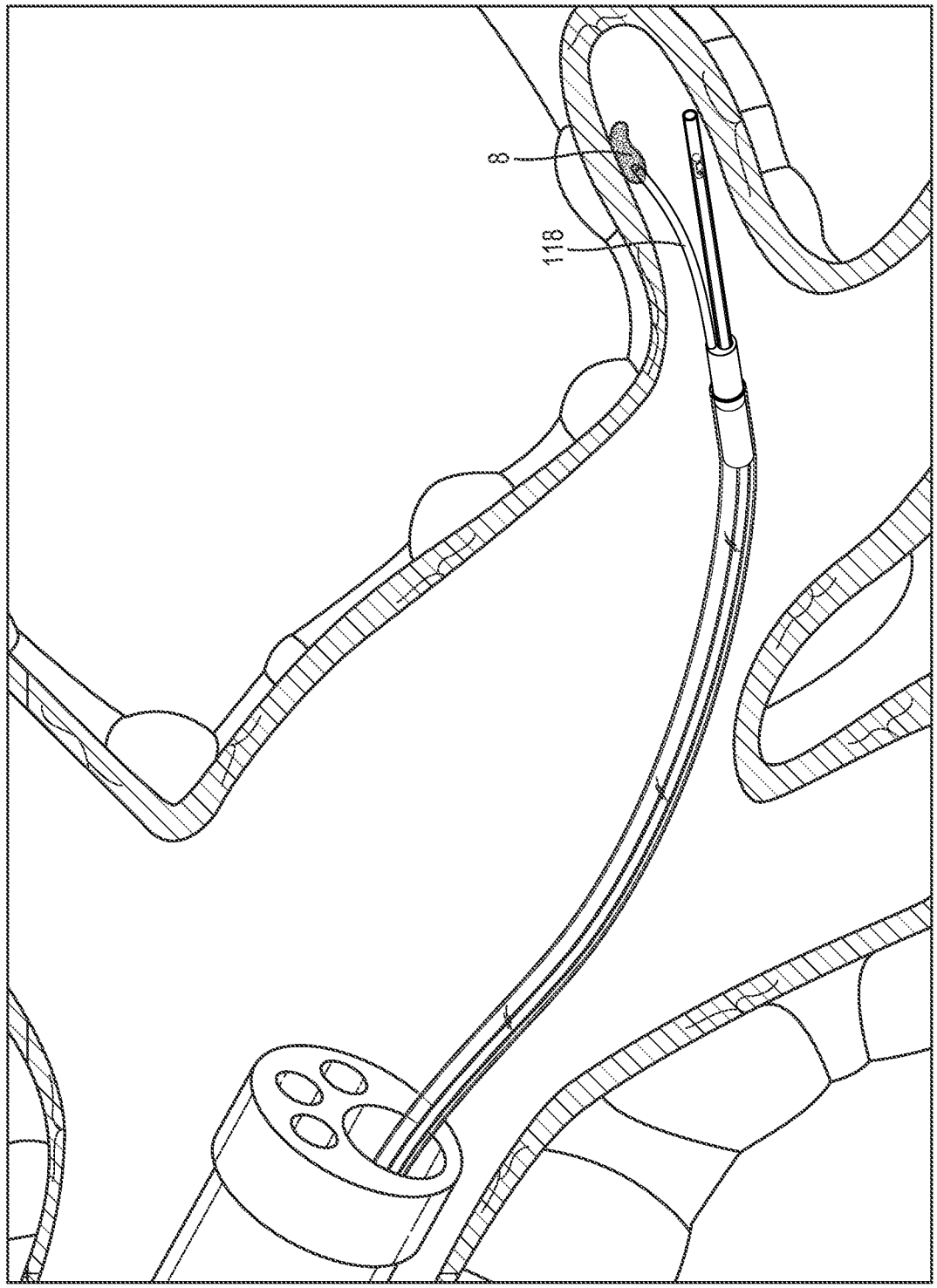

Referring to FIGS. 7A-7F, in use and by way of example, a bronchoscope 2 may be advanced through the trachea and into a bronchial passage in the vicinity of a target pulmonary nodule (FIG. 7A). Depending on the type of pulmonary nodule visualized through the bronchoscope (e.g., concentric or eccentric), an appropriate first component 110 (e.g., straight or curved, respectively) may be press-fitted onto the second component 120 already attached to the ultrasound catheter 130. The ultrasound transducer 136 may be positioned distally beyond the tip of the tissue sampling element 118 by advancing the MDU, as discussed above. The tissue sampling system 100 may then be proximally retracted to a predetermined position, e.g., by proximally retracting the sheath 140, to position the exterior tube 150 over the ultrasound catheter 130 (e.g., covering the distal end of the sheath 140 and ultrasound transducer 136) and tissue sampling element 118 of the first component 110. Enclosing the ultrasound transducer 136 and tissue sampling element 118 within the exterior tube 150 may protect the ultrasound transducer and prevent the tissue sampling element 118 from engaging the endoscope lumen and/or prematurely puncturing the lung tissue prior to identifying the target pulmonary nodule. The exterior tube 150 may then be advanced (e.g., threaded, pushed etc.) through and advanced distally beyond a working channel 4 of the bronchoscope 2 into the bronchial passage adjacent to the pulmonary nodule 8 (FIG. 7B). A proximal end (not depicted) of the sheath 140 (e.g., the portion that includes the braided material 140a) may then be distally advanced to position the ultrasound transducer 136 beyond (e.g., outside) the distal end 154 of the exterior tube 150 and provide an ultrasound image of the pulmonary nodule 8 (FIG. 7C). With the location and orientation of the pulmonary nodule 8 determined, the ultrasound probe 138 may be proximally retracted through the fixed sheath 140 via the MDU to position the ultrasound transducer 136 slightly behind (e.g., proximal to) the tip of the tissue sampling element 118 (FIG. 7D), thereby allowing the tissue sampling element 118 (and pulmonary nodule 8) to be visualized on the radial ultrasound image. The tissue sampling system 100 may be rotated as necessary to align the tissue sampling element 118 with the pulmonary nodule 8. Alternatively, rather than proximally retracting the ultrasound probe to visualize the tissue sampling element, the location of the tissue sampling element 118 relative to the ultrasound transducer 136 may be determined by visualizing a "strip" of hyperechoic material integrally formed within a portion of the sheath 140 on the radial ultrasound image. As above, the tissue sampling system may be rotated as necessary to align the tissue sampling element 118 with the pulmonary nodule 8 based on the position of the "strip" of hyperechoic material. The tissue sampling element 118 may then be advanced into the pulmonary nodule 8 by actuating a proximal end (not depicted) of the sheath 140 such that the ultrasound catheter 130, and attached first and second components 110, 120, move distally through the exterior tube 150 (FIG. 7E). The sheath 140 may be actuated (e.g., extended and retracted) as many times as necessary to obtain sufficient tissue sample within the tissue sampling element 118. Referring to FIG. 7F, a tissue sample may be obtained from an eccentric pulmonary nodule using a tissue sampling element 118 that includes a curved or bent configuration, as depicted in 4B. When the medical professional determines that the tissue sampling element 118 contains a sufficient amount of tissue sample for cytologic analysis, the proximal end (not depicted) of the sheath 140 may be proximally retracted to position the ultrasound transducer 136 and tissue sampling element 118 within the exterior tube 150. With the ultrasound transducer 136 and tissue sampling element 118 disposed (e.g., protected) within the exterior tube 150, the exterior tube 150 may be proximally retracted to remove the tissue sampling system 100 from the body passage and through the working channel of the endoscope.

Referring to FIG. 8A, after the tissue sampling system 100 has been removed from the patient, the first component 110 may be separated from the keyed or pressed-fit interlock with the second component 120. The tissue sampling element 118 may then be removed from the first component and attached to a corresponding fitting 80, e.g., luer-lock, of an ejection system 70 (FIG. 8B). For example, the ejection system 70 (e.g., stylet gun, syringe assembly etc.) may include a plunger 72 attached to an elongate stylet 74 which passes through a spring 76 housed within a chamber 78. In one embodiment, the recessed portion 113 may extend through (not shown) the length of the first component 110 such that a lumen of the tissue sampling element 118 aligns and is coextensive with the recessed portion 113. When the plunger 72 is depressed, the spring 76 moves to a compressed configuration within the chamber 78 and actuates the elongate stylet 74 to pass through the fitting 80 and lumen of the tissue sampling element 118 to eject the tissue sample 82 for cytologic analysis (FIG. 8C). Alternatively, the depressing the plunger may force a pulse of compressed air through the fitting 80 and lumen of the tissue sampling element (rather than a stylet) to eject the tissue sample.

The medical devices of the present disclosure are not limited to bronchoscopes, and may include a variety of medical devices for accessing body passageways, including, for example, catheters, ureteroscopes, duodenoscopes, colonoscopes, arthroscopes, cystoscopes, hysteroscopes, and the like. Alternatively, the tissue sampling system of the present disclosure may be positioned within the patient in the absence of an accompanying medical device.

Various components of the tissue sampling system (e.g., first component 110, second component 120, sheath 140, exterior tube 150) and ejection system 70, may be unitarily formed from suitable polymeric materials using extrusion (e.g., injection molding) and/or die-casting technologies, as are known in the art. Non-limiting examples of suitable materials may include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Ultraviolet curable polymers, such as polyimides and acrylic or methacrylic polymers and copolymers can also be used. Other examples of suitable polymers that can be used in balloons include polyethylenes, polyethylene ionomers, polyethylene copolymers, polyetheretherketone (PEEK), thermoplastic polyester elastomers (e.g., Hytrel®) and combinations thereof. In addition, or alternatively, any or all of these components may comprise metallic, ceramic or hardened plastic materials, as are known in the art.

The size, shape and/or configuration of the various components are not limited to those depicted in the figures. For example, the first and second components 110, 120, are not necessarily limited to the depicted circular and/or or oblong shapes and/or openings.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system, comprising:
    a first component, comprising:
        a proximal end;
        a distal end; and
        a lumen extending therebetween;
    a second component, comprising:
        a proximal end;
        a distal end; and
        a lumen extending therebetween;
    wherein the proximal end of the first component is removably attached to the distal end of the second component to form a contiguous lumen;
    an ultrasound catheter extending through the contiguous lumen of the first and second components; and
    an exterior tube slidably disposed about the first component, second component and ultrasound catheter.

2. The system of claim 1, wherein the ultrasound catheter comprises an ultrasound probe slidably disposed within a sheath, and wherein the sheath forms an interference fit with the lumen of the second component.

3. The system of claim 2, wherein a portion of the sheath extends distally beyond the ultrasound probe.

4. The system of claim 3, wherein the portion of the sheath that extends distally beyond the ultrasound probe includes an unbraided material.

5. The system of claim 2, wherein a portion of the sheath includes a braided material.

6. The system of claim 5, wherein the braided material extends along a proximal portion of the ultrasound probe.

7. The system of claim 2, wherein the sheath includes a proximal end, a distal end and a lumen extending therebetween.

8. The system of claim 7, wherein the lumen of the sheath includes a first diameter portion and a second diameter portion.

9. The system of claim 1, further comprising a tissue sampling element attached to the distal end of the first component.

10. The system of claim 1, wherein the proximal end of the first component includes a recessed portion configured to receive a post extending from the distal end of the second component.

11. The system of claim 10, wherein the post of the second component forms an interference fit with the recessed portion of the first component.

12. The system of claim 10, wherein the lumen of the first component aligns with the lumen of the second component to form the contiguous lumen when the post is disposed within the recessed portion.

13. The system of claim 1, further comprising a delivery device comprising a working channel configured to slidably receive the exterior tube.

14. An apparatus, comprising:
    a contiguous lumen comprising a lumen of a first component and a lumen of a second component, wherein a proximal end of the first component is removably attached to a distal end of the second component;
    an ultrasound catheter extending through the contiguous lumen; and
    an exterior tube slidably disposed about the contiguous lumen and the ultrasound catheter.

15. The apparatus of claim 14, wherein the ultrasound catheter comprises an ultrasound probe slidably disposed within a sheath, and wherein the sheath forms an interference fit with the lumen of the second component.

16. The apparatus of claim 14, further comprising a tissue sampling element attached to a distal end of the first component.

17. The apparatus of claim 14, wherein the proximal end of the first component includes a recessed portion configured to receive a post extending from the distal end of the second component.

18. The apparatus of claim 17, wherein the post of the second component forms an interference fit with the recessed portion of the first component.

19. A method, comprising:
    forming a contiguous lumen with a lumen of a first component and a lumen of a second component by removably attaching a proximal end of the first component to a distal end of the second component;
    extending an ultrasound catheter through the contiguous lumen; and
    slidably disposing an exterior tube about the first component, second component, and the ultrasound catheter.

20. The method of claim 19, comprising attaching a tissue sampling element to a distal end of the first component.

* * * * *